(12) United States Patent
Storck et al.

(10) Patent No.: US 7,592,294 B2
(45) Date of Patent: Sep. 22, 2009

(54) GAS PHASE OXIDATION CATALYST WITH DEFINED VANADIUM OXIDE PARTICLE SIZE DISTRIBUTION

(75) Inventors: Sebastian Storck, Mannheim (DE); Jürgen Zühlke, Speyer (DE); Samuel Neto, Mannheim (DE); Frank Rosowski, Mannheim (DE); Wolfgang Rummel, Köln (DE)

(73) Assignee: BASF SE, Ludwigshafen (DE)

( * ) Notice: Subject to any disclaimer, the term of this patent is extended or adjusted under 35 U.S.C. 154(b) by 250 days.

(21) Appl. No.: 10/573,481

(22) PCT Filed: Sep. 24, 2004

(86) PCT No.: PCT/EP2004/010749

§ 371 (c)(1),
(2), (4) Date: Nov. 8, 2006

(87) PCT Pub. No.: WO2005/030692

PCT Pub. Date: Apr. 7, 2005

(65) Prior Publication Data

US 2007/0093384 A1    Apr. 26, 2007

(30) Foreign Application Priority Data

Sep. 26, 2003 (DE) ................. 103 44 846

(51) Int. Cl.
*B01J 23/22* (2006.01)
*B01J 21/06* (2006.01)

(52) U.S. Cl. .................................... 502/353; 502/350

(58) Field of Classification Search ............. 502/350, 502/353
See application file for complete search history.

(56) References Cited

U.S. PATENT DOCUMENTS

| 3,464,930 A | 9/1969 | Friedrichsen et al. |
| 3,509,179 A | 4/1970 | Friedrichsen et al. |
| 3,898,249 A | 8/1975 | Felice et al. |
| 4,397,768 A | 8/1983 | Felice |
| 4,521,618 A | 6/1985 | Arntz et al. |
| 4,539,409 A | 9/1985 | Arntz et al. |
| 4,621,072 A | 11/1986 | Arntz et al. |
| 5,792,719 A | 8/1998 | Eberle et al. |
| 5,969,160 A | 10/1999 | Lindstrom |
| 6,528,683 B1 | 3/2003 | Heidemann et al. |
| 6,586,361 B1 | 7/2003 | Heidemann et al. |
| 6,700,000 B1 | 3/2004 | Heidemann et al. |
| 6,730,631 B1 | 5/2004 | Eberle et al. |

FOREIGN PATENT DOCUMENTS

| DE | 1442590 | 10/1968 |
| DE | 2005969 | 8/1971 |
| DE | 2106796 | 8/1972 |
| DE | 22 38 067 | 2/1974 |
| DE | 2550686 | 3/1977 |
| DE | 4006935 | 9/1991 |
| DE | 19633757 | 2/1998 |
| DE | 198 07 018 A1 | 8/1998 |
| DE | 19717344 A1 | 10/1998 |
| DE | 99/61433 | 12/1999 |
| DE | 198 24 532 A1 | 12/1999 |
| EP | 0 068 192 B1 | 8/1986 |
| EP | 539878 A2 | 5/1993 |
| EP | 0 744 214 B1 | 11/1996 |
| EP | 1181097 | 2/2002 |

OTHER PUBLICATIONS

Went et al. (1992) "Quantitative Structural Analysis of Dispersed Vanadia Species in TiO$_2$ (Anatase)-Supported V$_2$O$_5$" *Journal of Catalysis* 134, 479-491.
Monti et al., 1983. "Temperature-Programmed Reduction. Parametric Sensitivity and Estimation of Kinetic Parameters" *Journal of Catalysis* 83, 323-335.

*Primary Examiner*—Timothy C Vanoy
*Assistant Examiner*—Daniel Berns
(74) *Attorney, Agent, or Firm*—Connolly Bove Lodge & Hutz LLP

(57) ABSTRACT

A process is described for producing a catalyst for gas-phase oxidations, in which a suspension of TiO$_2$ and V$_2$O$_5$ particles is applied to a fluidized inert support, wherein at least 90% by volume of the V$_2$O$_5$ particles have a diameter of 20 µm or less and at least 95% by volume of the V$_2$O$_5$ particles have a diameter of 30 µm or less. The defined particle size distribution of the V$_2$O$_5$ allows a high coating efficiency.

15 Claims, No Drawings

GAS PHASE OXIDATION CATALYST WITH DEFINED VANADIUM OXIDE PARTICLE SIZE DISTRIBUTION

CROSS REFERENCE TO RELATED APPLICATION

The present application is a National Stage application of PCT/EP2004/010749, filed Sep. 24, 2004, which claims priority from German Patent Application No. DE 103 44 846.2, filed Sep. 26, 2003.

DESCRIPTION

The invention relates to a gas-phase oxidation catalyst which comprises titanium dioxide and vanadium oxide and has a defined vanadium oxide particle size distribution, to a process for producing it and to the use of the catalyst for preparing phthalic anhydride from o-xylene, naphthalene or mixtures thereof.

Many carboxylic acids and/or carboxylic anhydrides are prepared industrially by means of catalytic gas-phase oxidation of aromatic hydrocarbons such as benzene, the xylenes, naphthalene, toluene or durene in fixed-bed reactors. It is possible to obtain, for example, benzoic acid, maleic anhydride, phthalic anhydride, isophthalic acid, terephthalic acid or pyromellitic anhydride in this way. In general, a mixture of an oxygen-containing gas and the starting material to be oxidized is passed through tubes in which a bed of a catalyst is present. To regulate the temperature, the tubes are surrounded by a heat transfer medium, for example a salt melt.

Catalysts which have been found to be useful for these oxidation reactions are coated catalysts in which the catalytically active composition has been applied in the form of a shell to an inert support material such as steatite. The catalytically active constituents of the catalytically active composition of these coated catalysts are generally titanium dioxide and vanadium pentoxide. The catalytically active composition can further comprise small amounts of many other oxidic compounds which act as promoters to influence the activity and selectivity of the catalyst.

To produce such coated catalysts, an aqueous suspension of the constituents of the active composition and/or their precursor compounds is sprayed onto the support material at elevated temperature until the desired proportion by overall weight of active composition in the catalyst has been achieved.

DE-A 2550686 describes a process in which an aqueous solution comprising titanium tetrachloride and a vanadium (IV) salt is applied to a support.

In the production method disclosed in DE-A 1442590, finely divided titanium dioxide in the anatase modification is added to a solution of vanadyl oxalate, formamide and water. The resulting slurry is applied to inert catalyst supports.

WO 00/12214 describes a production process in which a mixture of titanium dioxide, vanadyl oxalate, an organic binder and, if appropriate, promoters is applied in a shell-like manner in two concentric layers to inert support rings by spraying on in a coating drum, coating in a fluidized bed or by powder coating.

EP-A 539878 describes the production of catalysts for preparing phthalic anhydride in the gas phase. Ammonium metavanadate is dissolved in aqueous oxalic acid solution and stirred together with promoters. $TiO_2$, prepared from titanium sulfate by the sulfate process is subsequently added. The resulting suspension is homogenized and sprayed at elevated temperature onto catalyst supports.

According to DE-A 2106796 and DE-A 19633757 an aqueous suspension of anatase and titanium dioxide hydrate, $V_2O_5$ and an organic binder component is applied to the supports.

The known production processes can be divided into two classes on the basis of the vanadium source used: in one case, a soluble vanadium(IV) compound such as vanadyl oxalate is used as vanadium source. The reduction to vanadium(IV) is effected by means of organic reducing agents such as oxalic acid. In the other case, insoluble vanadium(V) compounds such as $V_2O_5$ are added to the aqueous suspension. Since a reducing agent is no longer required here, the costs of starting materials are lower. However, a disadvantage is that the $V_2O_5$ particles tend to demix in a coating process in a fluidized bed and are not deposited completely on the support to be coated, but instead are partly carried out with, for example, the process air or settle as a deposit on the coating apparatus. To make up for the loss, an excess of $V_2O_5$ has to be used. It is desirable to keep the excess required as small as possible.

It is an object of the invention to provide an economical process for producing gas-phase oxidation catalysts comprising titanium dioxide and vanadium oxide and to provide the catalysts obtainable in this way.

It has now been found that the efficiency of the coating operation depends greatly on the particle size distribution of the $V_2O_5$ suspended in the coating suspension.

The invention provides a catalyst for gas-phase oxidations which comprises an inert support and, applied thereto, a catalytically active composition comprising from 1 to 40% by weight of vanadium oxide, calculated as $V_2O_5$, and from 60 to 99% by weight of titanium dioxide, calculated as $TiO_2$, and is obtainable by applying a suspension of $TiO_2$ and $V_2O_5$ particles to the support, wherein at least 90% by volume of the $V_2O_5$ particles have a diameter of 20 μm or less and at least 95% by volume of the $V_2O_5$ particles have a diameter of 30 μm or less.

The invention additionally provides a process for producing a catalyst for gas-phase oxidations, in which a suspension of $TiO_2$ and $V_2O_5$ particles is applied to a fluidized inert support, wherein at least 90% by volume of the $V_2O_5$ particles have a diameter of 20 μm or less and at least 95% by volume of the $V_2O_5$ particles have a diameter of 30 μm or less.

Preference is given to at least 90% by volume of the $V_2O_5$ particles having a diameter of 15 μm or less and at least 95% by volume of the $V_2O_5$ particles having a diameter of 20 μm or less.

In particularly preferred embodiments, at least 60% by volume of the $V_2O_5$ particles have a diameter of 4 μm or less, at least 80% by volume of the $V_2O_5$ particles have a diameter of 10 μm or less, at least 90% by volume of the $V_2O_5$ particles have a diameter of 15 μm or less and at least 95% by volume of the $V_2O_5$ particles have a diameter of 20 μm or less.

Preference is given to at least 50% by volume of the $V_2O_5$ particles having a diameter of more than 2 μm. The volume-based $D_{50}$ is preferably in the range from 2.0 to 2.5 μm.

The volume-based particle size distribution is, for the purposes of the present patent application, appropriately determined by means of laser light scattering and evaluation by the Fraunhofer method. In this method, parallel laser light is scattered by the particles. Each particle produces a scattering pattern characteristic of its size. The scattering spectrum is measured by means of detectors and the particle size distribution is calculated as a volume distribution by means of a microcomputer.

Vanadium oxides having a suitable particle size distribution can be produced by sufficiently long milling in suitable mills. Suitable mills include, for example, impact mills, roll mills, vibratory mills, milling media mills or tumbling mills. Milling media mills are preferred. They comprise a cylindrical working chamber which is mounted horizontally on bearings and rotates about a fixed point of rotation. The working chamber is charged with milling media of generally different sizes. The material to be milled is present in the gaps between the milling media. As milling media, use is made of wear-resistant forged or cast steel balls, rods or rod sections. Depending on the speed of rotation of the mill, particularly movements of the milling media and thus different stresses on the material to be milled, e.g. friction, shock, impact and pressure, will be established, as a result of which the relatively large particles of the material to be milled are broken up.

The catalytically active composition in the calcined state preferably comprises, based on the total amount of catalytically active composition, from 1 to 40% by weight of vanadium oxide, calculated as $V_2O_5$, and from 60 to 99% by weight of titanium dioxide, calculated as $TiO_2$. The catalytically active composition can further comprise up to 1% by weight of a cesium compound, calculated as Cs, up to 1% by weight of a phosphorus compound, calculated as P, and up to 10% by weight of antimony oxide, calculated as $Sb_2O_3$.

Apart from the optional additives cesium and phosphorus, it is in principle possible for small amounts of many other oxidic compounds which act as promoters to influence the activity and selectivity of the catalyst, for example by reducing or increasing its activity, to be present in the catalytically active composition. Examples of such promoters are the alkali metal oxides, in particular the abovementioned cesium oxide and also lithium, potassium and rubidium oxides, thallium(I)oxide, aluminum oxide, zirconium oxide, iron oxide, nickel oxide, cobalt oxide, manganese oxide, tin oxide, silver oxide, copper oxide, chromium oxide, molybdenum oxide, tungsten oxide, iridium oxide, tantalum oxide, niobium oxide, arsenic oxide, antimony oxide, cerium oxide. From this group, use is generally made of cesium as promoter.

Furthermore, among the promoters mentioned, the oxides of niobium and tungsten in amounts of from 0.01 to 0.50% by weight, based on the catalytically active composition, are preferred as additives. As additives which increase the activity but reduce the selectivity, oxidic phosphorus compounds, in particular phosphorus pentoxide, are especially useful.

The titanium dioxide used advantageously consists of a mixture of a $TiO_2$ having a BET surface area of from 5 to 15 $_{m2/g}$ and a $TiO_2$ having a BET surface area of from 15 to 50 $m^2/g$. It is also possible to use a single titanium dioxide having a BET surface area of from 5 to 50 m/g, preferably from 13 to 28 m/g.

As inert support material, it is possible to use virtually all support materials of the prior art as are advantageously employed in the production of coated catalysts for the oxidation of aromatic hydrocarbons to form aldehydes, carboxylic acids and/or carboxylic anhydrides, for example quartz ($SiO_2$), porcelain, magnesium oxide, tin dioxide, silicon carbide, rutile, alumina ($Al_2O_3$), aluminum silicate, steatite (magnesium silicate), zirconium silicate, cerium silicate or mixtures of these support materials. The support material is generally nonporous. For the purposes of the present invention the expression "nonporous" should be interpreted in the sense of "nonporous except for technically inconsequential amounts of pores", since a small number of pores may be unavoidably present in the support material which ideally should contain no pores. As advantageous support materials, particular mention may be made of steatite and silicon carbide. The shape of the support material is generally not critical for the precatalysts and coated catalysts of the invention.

For example, catalyst supports in the form of spheres, rings, pellets, spirals, tubes, extrudates or crushed material can be used. The dimensions of these catalyst supports correspond to those of catalyst supports customarily used for producing coated catalysts for the gas-phase partial oxidation of aromatic hydrocarbons. Preference is given to using steatite in the form of spheres having a diameter of from 3 to 6 mm or of rings having an external diameter of from 5 to 9 mm and a length of from 3 to 8 mm and a wall thickness of from 1 to 2 mm.

In the process of the invention, the layer(s) of the coated catalyst is/are applied by spraying a suspension of $TiO_2$ and $V_2O_5$, which may, if appropriate, contain sources of the abovementioned promoter elements, onto the fluidized support. Before the coating procedure, the suspension is preferably stirred for a sufficiently long time, e.g. from 2 to 30 hours, in particular from 12 to 25 hours, to break up agglomerates of the suspended solids and to obtain a homogeneous suspension. The suspension typically has a solids content of from 20 to 50% by weight. The suspension medium is generally aqueous, e.g. water itself or an aqueous mixture with a water-miscible organic solvent such as methanol, ethanol, isopropanol, formamide and the like.

In general, organic binders, preferably copolymers, advantageously in the form of an aqueous dispersion, of vinyl acetate-vinyl laurate, vinyl acetate-acrylate, styrene-acrylate or vinyl acetate-ethylene, are added to the suspension. The binders are commercially available as aqueous dispersions having a solids content of, for example, from 35 to 65% by weight. The amount of such binder dispersions used is generally from 2 to 45% by weight, preferably from 5 to 35% by weight, particularly preferably from 7 to 20% by weight, based on the weight of the suspension.

The support is fluidized in an ascending stream of gas, in particular air, in a fluidized-or moving-bed apparatus. The apparatuses usually comprise a conical or spherical container into which the fluidized gas is introduced from below or from above via a tube projecting downward. The suspension is sprayed into the fluidized bed from above, from the side or from below by means of nozzles. The use of a riser tube arranged centrally or concentrically around the downward projecting tube is advantageous. A relatively high gas velocity prevails within the riser tube and transports the support particles upward. In the outer ring, the gas velocity is only slightly above the loosening velocity. In this way, the particles are transported with a circular vertical motion. A suitable fluidized-bed apparatus is described, for example, in DE-A 4006935.

Coating of the catalyst support with the catalytically active composition is generally carried out at coating temperatures of from 20 to 500° C., either under atmospheric pressure or under reduced pressure. In general, coating is carried out at from 0° C. to 200° C., preferably from 20 to 150° C., in particular from 60 to 120° C.

The catalytically active composition can also be applied in two or more layers, with, for example, the inner layer or layers having an antimony oxide content of up to 15% by weight and the outer layer having an antimony oxide content which is from 50 to 100% lower. In general, the inner layer of the catalyst is phosphorus-containing and the outer layer is low in or free of phosphorus.

The thickness of the layer of catalytically active composition is generally from 0.02 to 0.2 mm, preferably from 0.05 to 0.15 mm. The proportion of active composition in the catalyst is usually from 5 to 25% by weight, mostly from 7 to 15% by weight.

As a result of thermal treatment of the resulting precatalyst at temperatures of from >200 to 500° C., the binder is driven off from the applied layer by thermal decomposition and/or combustion. The thermal treatment is preferably carried out in situ in the gas-phase oxidation reactor.

The catalysts of the invention are generally suitable for the gas-phase oxidation of aromatic $C_6$-$C_{10}$-hydrocarbons such as benzene, the xylenes, toluene, naphthalene or durene (1,2,4,5-tetramethylbenzene) to form carboxylic acids and/or carboxylic anhydrides such as maleic anhydride, phthalic anhydride, benzoic acid and/or pyromellitic anhydride.

For this purpose, the catalysts produced according to the invention are introduced into reaction tubes which are thermostated to the reaction temperature from the outside, for example by means of salt melts, and the reaction gas is passed over the prepared catalyst bed at temperatures of generally from 300 to 450° C., preferably from 320 to 420° C. and particularly preferably from 340 to 400° C., and a gauge pressure of generally from 0.1 to 2.5 bar, preferably from 0.3 to 1.5 bar, at a space velocity of generally from 750 to 5000 $h^{-1}$.

The reaction gas supplied to the catalyst is generally produced by mixing a gas which comprises molecular oxygen and may further comprise suitable reaction moderators and/or diluents such as steam, carbon dioxide and/or nitrogen in addition to oxygen with the aromatic hydrocarbon to be oxidized, with the gas comprising molecular oxygen generally being able to comprise from 1 to 100 mol %, preferably from 2 to 50 mol % and particularly preferably from 10 to 30 mol %, of oxygen, from 0 to 30 mol %, preferably from 0 to 10 mol %, of water vapor and from 0 to 50 mol %, preferably from 0 to 1 mol %, of carbon dioxide, balance nitrogen. To produce the reaction gas, the gas comprising molecular oxygen is generally loaded with from 30 g to 150 g of the aromatic hydrocarbon to be oxidized per standard $m^3$ of gas.

It has been found to be particularly advantageous to use catalysts which differ in their catalytic activity and/or the chemical makeup of their active composition in the catalyst bed. When two reaction zones are employed, the catalyst used in the first reaction zone, i.e. the reaction zone closest to the inlet for the reaction gas, preferably has a somewhat lower catalytic activity than the catalyst present in the second reaction zone, i.e. the reaction zone closest to the gas outlet. In general, the reaction is controlled by means of the temperature settings so that the major part of the aromatic hydrocarbon present in the reaction gas is reacted in maximum yield in the first zone. Preference is given to using from three- to five-zone catalyst systems, in particular three- and four-zone catalyst systems.

The invention is illustrated by the following examples.

Measurement of the particle size distribution was carried out using a Frisch particle sizer "Analysette 22" in the measurement range from 0.3 to 300 μm at a resolution of 62 channels. To carry out the measurement, the $V_2O_5$ sample was suspended in water and circulated by pumping through the measurement cell. The measurement time was 2 scans. Evaluation was carried out by the Fraunhofer method.

EXAMPLE 1

54.227 kg of anatase (BET surface area=9 $m^2$/g), 126.517 kg of anatase (BET surface area=20 $m^2$/g), 14.195 kg of $V_2O_5$, 3.549 kg of $Sb_2O_3$, 0.805 kg of cesium carbonate were suspended in 519.035 kg of deionized water and stirred to achieve a homogeneous distribution. The $V_2O_5$ had the following volume-based particle size distribution: 10% ≦0.58 μm; 20% ≦0.87 μm; 30% ≦1.20 μm; 40% ≦1.61 μm; 50% ≦2.21 μm; 60% ≦3.26 μm; 70% ≦5.52 μm; 80% ≦9.46 μm; 90% ≦14.92 μm; 95% ≦19.51 μm; 99.9% ≦169.33 μm. 80 kg of an organic binder comprising a copolymer of vinyl acetate and vinyl laurate in the form of a 50% strength dispersion were added to the suspension. 60 kg of the suspension were sprayed onto 150 kg of steatite rings (magnesium silicate) having dimensions of 7×7×4 mm (external diameter× height×internal diameter) and dried in a fluidized-bed coating apparatus. Coating was carried out at temperatures of 80-120° C. using an air flow of 6000 $m^3$/h.

Analysis of the catalysts calcined at 400° C. indicated a proportion of $V_2O_5$ in the active composition of 6.85% by weight. In contrast, the calculated theoretical $V_2O_5$ content of the ignited active composition is 7.12% by weight. There was a missing amount of 0.27% (absolute). To compensate for the $V_2O_5$ loss during the coating procedure and produce catalysts having the prescribed $V_2O_5$ contents, the amount of $V_2O_5$ in the suspension had to be increased by 0.543 kg.

COMPARATIVE EXAMPLE 2

Example 1 was repeated using $V_2O_5$ having the following volume-based particle size distribution: 10% ≦0.62 μm; 20% ≦0.93 μm; 30% ≦1.25 μm; 40% ≦1.63 μm; 50% ≦2.10 μm; 60% ≦2.76 μm; 70% ≦3.84 μm; 80% ≦6.27 μm; 90% ≦24.24 μm; 95% ≦46.58 μm; 99.9% ≦300 μm.

Analysis of the catalysts calcined at 400° C. indicated a proportion of $V_2O_5$ in the active composition of 5.55% by weight. Compared to the theoretical value of 7.12% by weight, there was a missing amount of 1.57% (absolute). To compensate for the $V_2O_5$ loss during the coating procedure and produce catalysts having the prescribed $V_2O_5$ contents, the amount of $V_2O_5$ in the suspension had to be increased by 3.134 kg.

The above examples show that the use of $V_2O_5$ having a defined particle size distribution makes it possible to reduce the amount required.

The invention claimed is:

1. A process for producing a catalyst for gas-phase oxidations, the process comprising: applying a suspension of $TiO_2$ and $V_2O_5$ particles to a fluidized inert support, wherein at least 90% by volume of the $V_2O_5$ particles have a diameter of 20 μm or less and at least 95% by volume of the $V_2O_5$ particles have a diameter of 30 μm or less.

2. The process according to claim 1, wherein at least 90% by volume of the $V_2O_5$ particles have a diameter of 15 μm or less and at least 95% by volume of the $V_2O_5$ particles have a diameter of 20 μm or less.

3. The process according to claim 1, wherein at least 50% by volume of the $V_2O_5$ particles have a diameter of more than 2 μm.

4. The process according to claim 1, wherein the suspension further comprises one or more elements selected from the group consisting of cesium, phosphorus and antimony source.

5. The process according to claim 1, wherein the catalyst includes a catalytically active composition comprising from 1 to 40% by weight of vanadium oxide, calculated as $V_2O_5$, and from 60 to 99% by weight of titanium dioxide, calculated as $TiO_2$.

6. The process according to claim 5, wherein the catalyst includes a catalytically active composition further comprising, based on the total amount of catalytically active composition, up to 1% by weight of a cesium compound, calculated as Cs, up to 1% by weight of a phosphorus compound, calculated as P, and up to 10% by weight of antimony oxide, calculated as $Sb_2O_3$.

7. The process according to claim 2, wherein at least 50% by volume of the $V_2O_5$ particles have a diameter of more than 2 μm.

8. The process according to claim 2, wherein the suspension further comprises one or more elements selected from cesium, phosphorus and antimony source.

9. The process according to claim 2, wherein the catalyst includes a catalytically active composition comprising from 1 to 40% by weight of vanadium oxide, calculated as $V_2O_5$, and from 60 to 99% by weight of titanium dioxide, calculated as $TiO_2$.

10. The process according to claim 4, wherein the catalyst includes a catalytically active composition comprising from 1 to 40% by weight of vanadium oxide, calculated as $V_2O_5$, and from 60 to 99% by weight of titanium dioxide, calculated as $TiO_2$.

11. The process according to claim 1, wherein the suspension further comprises a cesium compound, a phosphorus compound and antimony oxide.

12. The process according to claim 11, wherein the catalyst includes a catalytically active composition comprising:
   1-40% by weight of vanadium oxide, calculated as $V_2O_5$, and from 60 to 99% by weight of titanium dioxide, calculated as $TiO_2$;
   up to 1% by weight of a cesium compound, calculated as Cs, up to 1% by weight of a phosphorus compound, calculated as P; and
   up to 10% by weight of antimony oxide, calculated as $Sb_2O_3$.

13. A catalyst prepared by a process comprising:
   providing a suspension of $TiO_2$ and $V_2O_5$ particles, wherein at least 90% by volume of the $V_2O_5$ particles have a diameter of 20 μm or less and at least 95% by volume of the $V_2O_5$ particles have a diameter of 30 μm or less;
   and providing a fluidized support in a stream of flowing gas, and contacting the fluidized support with the suspension of $TiO_2$ and $V_2O_5$ particles to provide a supported catalyst, wherein the supported catalyst further comprises up to 1% by weight of a cesium compound, calculated as Cs, up to 1% by weight of a phosphorus compound, calculated as P, and up to 10% by weight of antimony oxide, calculated as $Sb_2O_3$, based on the total weight percent catalyst.

14. The catalyst according to claim 13, further comprising an outer layer with an $Sb_2O_3$ content by weight that is 50% to 100% lower than the $Sb_2O_3$ content by weight of an inner layer of the supported catalyst.

15. The catalyst according to claim 13, wherein the flowing gas is at a temperature of from 60° C. to 150° C.

* * * * *